(12) United States Patent
Endo et al.

(10) Patent No.: US 7,517,673 B2
(45) Date of Patent: Apr. 14, 2009

(54) PROCESS FOR PRODUCING ALPHA1,4-GALACTOSYLTRANSFERASE AND GALACTOSE-CONTAINING COMPLEX CARBOHYDRATE

(75) Inventors: Tetsuo Endo, Palo Alto, CA (US); Satoshi Koizumi, Tokyo (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 11/734,869

(22) Filed: Apr. 13, 2007

(65) Prior Publication Data

US 2008/0096254 A1 Apr. 24, 2008

Related U.S. Application Data

(62) Division of application No. 10/490,879, filed as application No. PCT/JP02/09908 on Sep. 26, 2002, now Pat. No. 7,232,674.

(30) Foreign Application Priority Data

Sep. 26, 2001 (JP) ............... 2001-292797

(51) Int. Cl.
C12P 19/00 (2006.01)
C12P 19/02 (2006.01)
C12N 9/10 (2006.01)
C12N 1/21 (2006.01)
C07H 21/04 (2006.01)

(52) U.S. Cl. .................... 435/72; 435/193; 435/252.33; 536/23.2

(58) Field of Classification Search ................. 435/193, 435/15, 69.1, 105, 252.33; 536/23.2
See application file for complete search history.

(56) References Cited

FOREIGN PATENT DOCUMENTS

| CA | 2 315 885 | 8/2001 |
|---|---|---|
| WO | WO 95/00595 | 1/1995 |
| WO | WO 00/61724 | 4/2000 |
| WO | WO-02/48320 | * 6/2002 |

OTHER PUBLICATIONS

Koizumi et al. Nat Biotechnol. Sep. 1998;16(9):847-50.*
Koizumi, et al., "Large-scale production of UDP-galactose and globotriose by coupling metabolically engineered bacteria", *Nature Biotechnology*, vol. 16, No. 9 (1998), pp. 847-850.
Wakarchuk, et al., "Role of paired basic residues in the expression of active recombinant galactosyltransferases from the . . . ", *Protein Engineering*, vol. 11, No. 4 (1998), pp. 295-302.
May, et al., Complete genomic sequence of *Pasteurella multocida*, Pm70, PNAS, vol. 98, No. 6 (2001), pp. 3460-3465.
Kojima, et al., "Molecular Cloning of Globotriaosylceramide/CD77 Synthase, a . . . ", *The Journal of Biological Chemistry*, vol. 275, No. 20 (2000), pp. 15152-15156.
Keusch, et al., "Cloning of $Gb_3$ Synthase, the Key Enzyme in Globo-series . . . ", *The Journal of Biological Chemistry*, vol. 275, No. 33 (2000), pp. 25315-25321.
Steffensen, et al., "Cloning and Expression of the Hist-blood Group $P^k$ UDP-galactose:Galβ-4Glbcβ1-Cer . . . ", *The Journal of Biological Chemistry*, vol. 276, No. 22 (2000), pp. 16723-16729.
Endo, et al., "Large-scale production of oligosaccharides using engineered bacteria", *Current Opinion in Structural Biology*, vol. 10, No. 5 (2000), pp. 536-541.
Johnson, "Synthesis of oligosaccharides by bacterial enzymes", Glycoconjugate Journal, vol. 16 (1999), pp. 141-145.

* cited by examiner

*Primary Examiner*—Nashaat T Nashed
*Assistant Examiner*—Iqbal H Chowdhury
(74) *Attorney, Agent, or Firm*—Fitzpatrick, Cella, Harper & Scinto (57) ABSTRACT

The present invention can provide a process for producing a protein having α1.4-galactosyltransferase activity using a transformant comprising a DNA encoding a protein having α1.4-galactosyltransferase activity derived from a microorganism belonging to the genus *Pasteurella* and a process for producing a galactose-containing complex carbohydrate using a transformant capable of producing a protein having α1.4-galactosyltransferase activity derived from a microorganism.

8 Claims, 1 Drawing Sheet

Fig. 1

SEQUENCE LISTING

<160> NUMBER OF SEQ ID NOS: 4

<210> SEQ ID NO 1
<211> LENGTH: 302
<212> TYPE: PRT
<213> ORGANISM: Pasteurella multocida

<400> SEQUENCE: 1

Met Asn Ile Leu Phe Val Ser Asp Asp Val Tyr Ala Arg His Leu Val
 1               5                  10                  15

Val Ala Ile Lys Ser Ile Ile Asn His Asn Glu Lys Gly Ile Ser Phe
            20                  25                  30

Tyr Ile Phe Asp Leu Gly Ile Lys Asp Glu Asn Lys Arg Asn Ile Asn
        35                  40                  45

Asp Ile Val Ser Ser Tyr Gly Ser Glu Val Asn Phe Ile Ala Val Asn
    50                  55                  60

Glu Lys Glu Phe Glu Ser Phe Pro Val Gln Ile Ser Tyr Ile Ser Leu
65                  70                  75                  80

Ala Thr Tyr Ala Arg Leu Lys Ala Ala Glu Tyr Leu Pro Asp Asn Leu
                85                  90                  95

Asn Lys Ile Ile Tyr Leu Asp Val Asp Val Leu Val Phe Asn Ser Leu
            100                 105                 110

Glu Met Leu Trp Asn Val Asp Val Asn Asn Phe Leu Thr Ala Ala Cys
        115                 120                 125

Tyr Asp Ser Phe Ile Glu Asn Glu Lys Ser Glu His Lys Lys Ser Ile
    130                 135                 140

Ser Met Ser Asp Lys Glu Tyr Tyr Phe Asn Ala Gly Val Met Leu Phe
145                 150                 155                 160

Asn Leu Asp Glu Trp Arg Lys Met Asp Val Phe Ser Arg Ala Leu Asp
                165                 170                 175

Leu Leu Ala Met Tyr Pro Asn Gln Met Ile Tyr Gln Asp Gln Asp Ile
            180                 185                 190

Leu Asn Ile Leu Phe Arg Asn Lys Val Cys Tyr Leu Asp Cys Arg Phe
        195                 200                 205

Asn Phe Met Pro Asn Gln Leu Glu Arg Ile Lys Gln Tyr His Lys Gly
    210                 215                 220

Lys Leu Ser Asn Leu His Ser Leu Glu Lys Thr Thr Met Pro Val Val
225                 230                 235                 240

Ile Ser His Tyr Cys Gly Pro Glu Lys Ala Trp His Ala Asp Cys Lys
                245                 250                 255

His Phe Asn Val Tyr Phe Tyr Gln Lys Ile Leu Ala Glu Ile Thr Arg
            260                 265                 270

Gly Thr Asp Lys Glu Arg Val Leu Ser Ile Lys Thr Tyr Leu Lys Ala
        275                 280                 285

Leu Ile Arg Arg Ile Arg Tyr Lys Phe Lys Tyr Gln Val Tyr
    290                 295                 300

<210> SEQ ID NO 2
<211> LENGTH: 906
<212> TYPE: DNA
<213> ORGANISM: Pasteurella multocida

<400> SEQUENCE: 2 atg aat att tta ttt gtt tct gat gat gtt tat gct aga cat ctg gtg      48
Met Asn Ile Leu Phe Val Ser Asp Asp Val Tyr Ala Arg His Leu Val

```
                 1               5                  10                 15
gtt  gcg  att  aaa  agc  att  ata  aat  cat  aat  gaa  aaa  ggt  att  tca  ttt      96
Val  Ala  Ile  Lys  Ser  Ile  Ile  Asn  His  Asn  Glu  Lys  Gly  Ile  Ser  Phe
               20                  25                 30 tat  att  ttt  gat  ttg  ggt  ata  aag  gat  gaa  aat  aag  aga  aat  att  aat     144
Tyr  Ile  Phe  Asp  Leu  Gly  Ile  Lys  Asp  Glu  Asn  Lys  Arg  Asn  Ile  Asn
               35                  40                 45 gat  att  gtt  tct  tct  tat  gga  agt  gaa  gtc  aac  ttt  att  gct  gtg  aat     192
Asp  Ile  Val  Ser  Ser  Tyr  Gly  Ser  Glu  Val  Asn  Phe  Ile  Ala  Val  Asn
     50                  55                  60 gag  aaa  gaa  ttt  gag  agt  ttt  cct  gtt  caa  att  agt  tat  att  tct  tta     240
Glu  Lys  Glu  Phe  Glu  Ser  Phe  Pro  Val  Gln  Ile  Ser  Tyr  Ile  Ser  Leu
65                  70                   75                      80 gca  aca  tat  gca  agg  cta  aaa  gcg  gca  gag  tat  ttg  ccg  gat  aat  tta     288
Ala  Thr  Tyr  Ala  Arg  Leu  Lys  Ala  Ala  Glu  Tyr  Leu  Pro  Asp  Asn  Leu
                    85                  90                  95 aat  aaa  att  att  tat  tta  gat  gtt  gat  gtt  ttg  gtt  ttt  aac  tca  tta     336
Asn  Lys  Ile  Ile  Tyr  Leu  Asp  Val  Asp  Val  Leu  Val  Phe  Asn  Ser  Leu
                    100                 105                 110 gaa  atg  tta  tgg  aat  gtt  gat  gtt  aat  aat  ttt  ctt  acc  gcg  gcc  tgt     384
Glu  Met  Leu  Trp  Asn  Val  Asp  Val  Asn  Asn  Phe  Leu  Thr  Ala  Ala  Cys
               115                 120                 125 tat  gat  tct  ttc  atc  gaa  aat  gaa  aag  tct  gag  cat  aaa  aaa  tcg  att     432
Tyr  Asp  Ser  Phe  Ile  Glu  Asn  Glu  Lys  Ser  Glu  His  Lys  Lys  Ser  Ile
               130                 135                 140 tca  atg  tca  gat  aag  gaa  tat  tat  ttt  aat  gca  gga  gta  atg  cta  ttt     480
Ser  Met  Ser  Asp  Lys  Glu  Tyr  Tyr  Phe  Asn  Ala  Gly  Val  Met  Leu  Phe
145                 150                 155                      160 aat  tta  gat  gaa  tgg  cgg  aag  atg  gat  gta  ttc  tca  aga  gct  tta  gac     528
Asn  Leu  Asp  Glu  Trp  Arg  Lys  Met  Asp  Val  Phe  Ser  Arg  Ala  Leu  Asp
                    165                 170                 175 ctg  tta  gct  atg  tat  cct  aat  caa  atg  att  tat  cag  gat  caa  gat  ata     576
Leu  Leu  Ala  Met  Tyr  Pro  Asn  Gln  Met  Ile  Tyr  Gln  Asp  Gln  Asp  Ile
                    180                 185                 190 ttg  aat  atc  ctt  ttt  agg  aat  aaa  gtc  tgt  tat  tta  gat  tgc  aga  ttt     624
Leu  Asn  Ile  Leu  Phe  Arg  Asn  Lys  Val  Cys  Tyr  Leu  Asp  Cys  Arg  Phe
               195                 200                 205 aat  ttc  atg  cca  aat  caa  ctt  gaa  aga  ata  aaa  caa  tac  cat  aaa  gga     672
Asn  Phe  Met  Pro  Asn  Gln  Leu  Glu  Arg  Ile  Lys  Gln  Tyr  His  Lys  Gly
               210                 215                 220 aaa  ttg  agc  aac  tta  cat  tct  tta  gaa  aaa  aca  acg  atg  cct  gtc  gtt     720
Lys  Leu  Ser  Asn  Leu  His  Ser  Leu  Glu  Lys  Thr  Thr  Met  Pro  Val  Val
225                 230                 235                      240 att  tca  cat  tat  tgt  ggt  cca  gaa  aaa  gcg  tgg  cat  gcg  gat  tgt  aaa     768
Ile  Ser  His  Tyr  Cys  Gly  Pro  Glu  Lys  Ala  Trp  His  Ala  Asp  Cys  Lys
                    245                 250                 255 cat  ttt  aat  gta  tat  ttc  tat  cag  aaa  ata  tta  gca  gaa  ata  acg  aga     816
His  Phe  Asn  Val  Tyr  Phe  Tyr  Gln  Lys  Ile  Leu  Ala  Glu  Ile  Thr  Arg
                    260                 265                 270 ggc  acg  gat  aaa  gaa  cgc  gta  tta  tct  ata  aaa  act  tat  ctc  aag  gcc     864
Gly  Thr  Asp  Lys  Glu  Arg  Val  Leu  Ser  Ile  Lys  Thr  Tyr  Leu  Lys  Ala
               275                 280                 285 ttg  att  aga  agg  att  aga  tat  aaa  ttc  aaa  tat  caa  gtc  tat                906
Leu  Ile  Arg  Arg  Ile  Arg  Tyr  Lys  Phe  Lys  Tyr  Gln  Val  Tyr
     290                 295                 300
```

<210> SEQ ID NO 3
<211> LENGTH: 27
<212> TYPE: DNA
<213> ORGANISM: Artificial Sequence -continued

```
<220> FEATURE:
<223> OTHER INFORMATION: Description of Artificial Sequence:Synthetic
      DNA

<400> SEQUENCE: 3
tgagaagctt tatgaatatt ttatttg                                              27

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 4
acaaggatcc aatagttaat agacttga                                             28
```

PROCESS FOR PRODUCING ALPHA1,4-GALACTOSYLTRANSFERASE AND GALACTOSE-CONTAINING COMPLEX CARBOHYDRATE

This application is a division of application Ser. No. 10/490,879 filed Mar. 26, 2004 (now U.S. Pat. No. 7,232,674), which in turn is a 371 of international PCT Application No. PCT/JP02/09908 filed Sep. 26, 2002.

TECHNICAL FIELD

The present invention relates to a process for producing a protein having α1,4-galactosyltransferase activity using a transformant comprising a DNA encoding a protein having α1,4-galactosyltransferase activity and a process for producing a galactose-containing complex carbohydrate using the transformant.

BACKGROUND ART

As α1,4-galactosyltransferase and its genes, genes derived from animals [*J. Biol. Chem.*, 275, 15152 (2000), *J. Biol. Chem.*, 275, 16723 (2000), *Biochem. Biophys. Res. Commun.*, 227, 909 (1996)] and the like have been obtained. However, there is no example in which the α1,4-galactosyltransferase derived from an animal was expressed in a microorganism, such as *Escherichia coli*, as a protein having activity.

On the other hand, in the case of microorganisms, there is a report in which a gene encoding the α1,4-galactosyltransferase was obtained from a microorganism belonging to the genus *Neisseria* and the α1,4-galactosyltransferase was expressed in *Escherichia coli* using the gene [*Protein Eng.*, 11, 295 (1998), *Nat. Biotechnol.*, 16, 847 (1998)]. However, there is no report in which the gene is obtained from a microorganism belonging to the genus *Pasteurella*.

Also, full nucleotide sequence of genomic DNA in *Pasteurella multocida* PM70 has been determined [*Proc. Natl. Acad. Sci. USA*, 98, 3460 (2001)], and it has been suggested that pm1139 gene is a gene encoding α1,4-galactosyltransferase by homology search and the like. However, there is no report that the gene product has α1,4-galactosyltransferase activity.

Among galactose-containing complex carbohydrates, especially, globotriose (Galα1,4Galβ1,4Glc) is a sugar part of globotriacylceramide (Gb3: Galα1,4Galβ-1,4Glc-Cer) which is widely distributed as a Pk-type complex carbohydrate, and is known as an acceptor complex carbohydrate of vero toxin of *Escherichia coli* O-157 and as an acceptor of Shiga toxin produced by *Shigella* sp. or enteroinvasive *Escherichia coli* [*J. Biol. Chem.*, 262, 8834 (1987), *Infect. Immun.*, 58, 611 (1990)]. Also, pharmaceuticals in which the sugar part is bound to a carrier and the like have been developed.

DISCLOSURE OF THE INVENTION

Objects of the present invention are to provide a process for producing a protein having α1,4-galactosyltransferase activity using a transformant comprising a DNA encoding a protein having α1,4-galactosyltransferase activity and a process for producing a galactose-containing complex carbohydrate using the transformant.

In order to solve the above problems, the present inventors have conducted intensive studies and found that pm1139 gene product having homology with a known α1,4-galactosyltransferase has actually α1,4-galactosyltransferase activity, and obtained the DNA, and thus the present invention has been completed.

Specifically, the present invention relates to the following (1) to (29):

(1) A process for producing a protein having α1,4-galactosyltransferase activity, which comprises: culturing a transformant capable of producing a protein having α1,4-galactosyltransferase activity derived from a microorganism belonging to the genus *Pasteurella* in a medium to produce and accumulate the protein having α1,4-galactosyltransferase activity in the culture, and recovering the protein from the culture.

(2) The process according to (1), wherein the microorganism belonging to the genus *Pasteurella* is *Pasteurella multocida*.

(3) The process according to (1), wherein the protein having α1,4-galactosyltransferase activity is a protein comprising the amino acid sequence represented by SEQ ID NO:1.

(4) The process according to (1), wherein the protein having α1,4-galactosyltransferase activity is a protein which consists of an amino acid sequence in which at least one amino acid is deleted, substituted or added in the amino acid sequence represented by SEQ ID NO:1, and has α1,4-galactosyltransferase activity.

(5) The process according to (1), wherein the protein having α1,4-galactosyltransferase activity is a protein which has an identity of at least 80% with the amino acid sequence represented by SEQ ID NO:1, and has α1,4-galactosyltransferase activity.

(6) The process according to (1), wherein the transformant is a transformant which comprises a recombinant DNA comprising a DNA encoding a protein having α1,4-galactosyltransferase activity.

(7) The process according to (6), wherein the transformant is obtained by using a microorganism as a host cell.

(8) The process according to (7), wherein the microorganism is *Escherichia coli*.

(9) The process according to (6), wherein the DNA encoding the protein having α1,4-galactosyltransferase activity is a DNA comprising the nucleotide sequence represented by SEQ ID NO:2.

(10) The process according to (6), wherein the DNA encoding the protein having α1,4-galactosyltransferase activity is a DNA which hybridizes with a DNA comprising the nucleotide sequence represented by SEQ ID NO:2 under stringent conditions, and encodes a protein having α1,4-galactosyltransferase activity.

(11) A process for producing a galactose-containing complex carbohydrate, which comprises: allowing a culture of a transformant capable of producing a protein having α1,4-galactosyltransferase activity or a treated product of the culture as an enzyme source, uridine-5'-diphosphogalactose and an acceptor complex carbohydrate to be present in an aqueous medium to produce and accumulate the galactose-containing complex carbohydrate in the aqueous medium, and recovering the galactose-containing complex carbohydrate from the aqueous medium.

(12) The process according to (11), wherein the treated product of the culture is selected from the group consisting of a concentrated product of the culture, a dried product of the culture, cells obtained by centrifuging the culture, a dried product of the cells, a freeze-dried product of the cells, a surfactant-treated product of the cells, an ultrasonic-treated product of the cells, a mechanically disrupted product of the cells, a solvent-treated product of the cells, an enzyme-treated product of the cells, a protein fraction of the cells, an immobilized product of the cells and an enzyme preparation obtained by extracting from the cells.

(13) The process according to (11), wherein the acceptor complex carbohydrate is a complex carbohydrate comprising an oligosaccharide having galactose in its non-reducing terminal.

(14) The process according to (13), wherein the oligosaccharide having galactose in the non-reducing terminal is an oligosaccharide selected from the group consisting of lactose, N-acetyllactosamine, lacto-N-tetraose, para-lacto-N-neohexaose and lacto-N-neotetraose.

(15) The process according to (11), wherein the acceptor complex carbohydrate is a complex carbohydrate selected from the group consisting of lactose, N-acetyllactosamine, lacto-N-tetraose, para-lacto-N-neohexaose and lacto-N-neotetraose.

(16) The process according to (11), wherein the protein having α1,4-galactosyltransferase is a protein derived from a microorganism belonging to the genus *Pasteurella*.

(17) The process according to (16), wherein the microorganism belonging to the genus *Pasteurella* is *Pasteurella multocida*.

(18) The process according to (11), wherein the protein having α1,4-galactosyltransferase activity is a protein comprising the amino acid sequence represented by SEQ ID NO:1.

(19) The process according to (11), wherein the protein having α1,4-galactosyltransferase activity is a protein which consists of an amino acid sequence in which at least one amino acid is deleted, substituted or added in the amino acid sequence represented by SEQ ID NO:1, and has α1,4-galactosyltransferase activity.

(20) The process according to (11), wherein the protein having α-1,4-galactosyltransferase activity is a protein which has an identity of at least 80% with the amino acid sequence represented by SEQ ID NO:1, and has α1,4-galactosyltransferase activity.

(21) The process according to (11), wherein the transformant is a transformant which comprises a recombinant DNA comprising a DNA encoding a protein having α1,4-galactosyltransferase activity.

(22) The process according to (21), wherein the transformant is obtained by using a microorganism as a host cell.

(23) The process according to (22), wherein the microorganism is *Escherichia coli*.

(24) The process according to (21), wherein the DNA encoding the protein having α1,4-galactosyltransferase activity is a DNA comprising the nucleotide sequence represented by SEQ ID NO:2.

(25) The process according to (21), wherein the DNA encoding the protein having α1,4-galactosyltransferase activity is a DNA which hybridizes with a DNA comprising the nucleotide sequence represented by SEQ ID NO:2 under stringent conditions, and encodes a protein having α1,4-galactosyltransferase activity.

(26) A protein having α1,4-galactosyltransferase activity, which comprises the amino acid sequence represented by SEQ ID NO:1.

(27) A protein which consists of an amino acid sequence in which at least one amino acid is deleted, substituted or added in the amino acid sequence represented by SEQ ID NO:1, and has α1,4-galactosyltransferase activity.

(28) A protein which has an identity of at least 80% with the amino acid sequence represented by SEQ ID NO:1, and has α1,4-galactosyltransferase activity.

(29) A DNA which hybridizes with the DNA comprising the nucleotide sequence represented by SEQ ID NO:2 under stringent condition and encodes a protein having α1,4-galactosyltransferase activity.

The present invention is explained below in detail.

The protein having α1,4-galactosyltransferase activity of the present invention includes the protein having α1,4-galactosyltransferase activity derived from a microorganisms belonging to the genus *Pasteurella*, preferably the protein having α1,4-galactosyltransferase activity derived from *Pasteurella multocida*.

The protein having α1,4-galactosyltransferase activity used in the process for producing a galactose-containing complex carbohydrate of the present invention is not particularly limited, so long as it is a protein having α1,4-galactosyltransferase activity. It is preferably a protein having α1,4-galactosyltransferase activity derived from a microorganism belonging to the genus *Pasteurella*, and more preferably a protein having α1,4-galactosyltransferase activity derived from *Pasteurella multocida*.

Specifically, the protein includes a protein comprising the amino acid sequence represented by SEQ ID NO:1; a protein which consists of an amino acid sequence in which at least one amino acid is deleted, substituted or added in the amino acid sequence represented by SEQ ID NO:1, and has α1,4-galactosyltransferase activity; and a protein which has an identity of at least 80% with the amino acid sequence represented by SEQ ID NO:1, and has α1,4-galactosyltransferase activity.

The protein which consists of an amino acid sequence in which at least one amino acid is deleted, substituted or added, and has α1,4-galactosyltransferase activity can be obtained, for example, by introducing mutation(s) to a DNA encoding a protein comprising the amino acid sequence represented by SEQ ID NO:1 according to a method for introducing site-directed mutagenesis described in *Molecular Cloning, A Laboratory Manual*, Second Edition, Cold Spring Harbor Laboratory Press (1989) (hereinafter referred to as "*Molecular Cloning*, Second Edition"); *Current Protocols in Molecular Biology*, John Wiley & Sons (1987-1997) (hereinafter referred to as "*Current Protocols in Molecular Biology*"); *Nucleic Acids. Research*, 10, 6487 (1982); *Proc. Natl. Acad. Sci. USA*, 79, 6409 (1982); *Gene*, 34, 315 (1985); *Nucleic Acids. Research*, 13, 4431 (1985); *Proc. Natl. Acad. Sci. USA*, 82, 488 (1985) and the like.

The number of the amino acids which are deleted, substituted or added is not particularly limited; however, it is such a number that deletion, substitution or addition can be carried out by a known method such as method for introducing site-directed mutagenesis. The number is 1 to several tens, preferably 1 to 20, more preferably 1 to 10, and most preferably 1 to 5.

The deletion, substitution or addition of at least one amino acid residue in the amino acid sequence represented by SEQ ID NO:1 means that one or at least two amino acids are deleted, substituted or added at any position in the same sequence. The deletion, substitution or addition can be car- 
ried out in the same amino acid sequence simultaneously. Also, the amino acid residue substituted or added can be natural or non-natural. The natural amino acid residue includes L-alanine, L-asparagine, L-aspartic acid, L-glutamine, L-glutamic acid, glycine, L-histidine, L-isoleucine, L-leucine, L-lysine, L-arginine, L-methionine, L-phenylalanine, L-proline, L-serine, L-threonine, L-tryptophan, L-tyrosine, L-valine, L-cysteine, and the like.

Herein, examples of amino acid residues which are substituted with each other are shown below. Amino acid residues in the same group can readily be substituted with each other.

Group A:
leucine, isoleucine, norleucine, valine, norvaline, alanine, 2-aminobutanoic acid, methionine, O-methylserine, t-butylglycine, t-butylalanine, cyclohexylalanine;

Group B:
aspartic acid, glutamic acid, isoasparatic acid, isoglutamic acid, 2-aminoadipic acid, 2-aminosuberic acid;

Group C:
asparagine, glutamine;

Group D:
lysine, arginine, ornithine, 2,4-diaminobutanoic acid, 2,3-diaminopropionic acid;

Group E:
proline, 3-hydroxyproline, 4-hydroxyproline;

Group F:
serine, threonine, homoserine;

Group G:
phenylalanine, tyrosine.

Also, in order that the protein which consists of an amino acid sequence in which at least one amino acid is deleted, substituted or added has α1,4-galactosyltransferase activity, the protein has an identity of preferably at least 60% or more, more preferably 80% or more, and most preferably 95% or more, with the amino acid sequence represented by SEQ ID NO:1.

The identity of an amino acid sequence or a nucleotide sequence can be determined by using the algorithm BLAST by Karlin and Altschul [*Proc. Natl. Acad. Sci. USA*, 90, 5873 (1993)] or FASTA [*Methods Enzymol.*, 183, 63 (1990)]. The programs called BLASTN and BLASTX have developed based on the above algorithm BLAST [*J. Mol. Biol*, 215, 403 (1990)]. In the case of analyzing a nucleotide sequence by BLASTN based on BLAST, for example, the parameter can be set to score=100, wordlength=12. Also, in the case of analyzing an amino acid sequence by BLASTX based on BLAST, for example, the parameter can be set to score=50, wordlength=3. When BLAST and Gapped BLAST programs are used, a default parameter of each program can be used. The specific analysis methods of using the above programs are known.

The transformant used in the production of the protein having α1,4-galactosyltransferase activity of the present invention includes a transformant comprising a DNA encoding a protein having α1,4-galactosyltransferase. The DNA encoding the protein having α1,4-galactosyltransferase includes (1) a DNA encoding a protein comprising the amino acid sequence represented by SEQ ID NO:1;

(2) a DNA comprising the nucleotide sequence represented by SEQ ID NO:2;

(3) a DNA encoding a protein which consists of an amino acid sequence in which at least one amino acid is deleted, substituted or added in the amino acid sequence represented by SEQ ID NO:1, and has α1,4-galactosyltransferase activity;

(4) a DNA encoding a protein which has an identity of at least 80% with the amino acid sequence represented by SEQ ID NO:1, and has α1,4-galactosyltransferase activity; and (5) a DNA which hybridizes with a DNA comprising the nucleotide sequence represented by SEQ ID NO:2 under stringent conditions, and encodes a protein having α1,4-galactosyltransferase activity.

The DNA which is hybridizable under stringent conditions is a DNA obtained by colony hybridization, plaque hybridization, Southern hybridization or the like using, as a probe, a part or a full length of a DNA comprising the nucleotide sequence represented by SEQ ID NO:2. Specifically, the DNA includes a DNA which can be identified by carrying out hybridization at 65° C. in the presence of 0.7-1.0 mol/l NaCl using a filter on which a DNA prepared from colonies or plaques is immobilized, and then washing the filter with 0.1× to 2×SSC solution (the composition of 1×SSC solution contains 150 mmol/l sodium chloride and 15 mmol/l sodium citrate) at 65° C. The hybridization can be carried out in accordance with a known method described in, for example, *Molecular Cloning*, Second Edition; *Current Protocols in Molecular Biology*; *DNA Cloning 1: Core Techniques, A Practical Approach*, Second Edition, Oxford University (1995) or the like. Specifically, the DNA which is hybridizable includes a DNA having an identity of at least 60% or more, preferably 80% or more, and more preferably 95% or more, with the nucleotide sequence represented by SEQ ID NO:2 when calculated based on the above parameters using above BLAST, FASTA or the like.

[1] Preparation of a DNA Used in the Process for Producing the Present Invention (1) Selection of a DNA Encoding the Protein Having α1,4-galactosyltransferase Activity Using Database The full nucleotide sequence of the genomic DNA in *Pasteurella multocida* PM70 was determined [*Proc. Natl. Acad. Sci., USA*, 98, 3460 (2001)], and the DNA encoding the protein having α1,4-galactosyltransferase activity can be selected by carrying out gene search, homology search and the like by using a known sialyltransferase gene based on the nucleotide sequence of the genomic DNA.

(2) Preparation of a DNA Used in the Production Process of the Present Invention The DNA encoding the protein having α1,4-galactosyltransferase activity used in the production process of the present invention can be prepared from a microorganism belonging to the genus *Pasteurella*. The microorganism belonging to the genus *Pasteurella* includes *Pasteurella multocida*, and specifically *Pasteurella multocida* PM70 (available from Minnesota University) and the like.

The microorganism belonging to *Pasteurella multocida* can be cultured by a known method [for example, *FEMS Microbiol. Lett.,* 166, 289 (1998)].

After the culturing, a chromosomal DNA of the microorganism can be isolated and purified by a known method (for example, method described in *Current Protocols in Molecular Biology*).

A DNA fragment containing the DNA used in the process for producing the present invention can be obtained by preparing a primer based on the nucleotide sequence of the genomic DNA selected in the item (1) and then carrying out PCR [*PCR Protocols*, Academic Press (1990)] using the genomic DNA as a template.

Furthermore, the DNA of interest can be obtained according to a hybridization method by using the synthetic DNA designed based on the nucleotide sequence of the genomic DNA as a probe.

The nucleotide sequence of the DNA can be determined by inserting the obtained DNA as it is or after digestion with an appropriate restriction enzyme, into a vector according to the usual method, and carrying out analysis by the generally used nucleotide sequence analysis method such as the dideoxy method [*Proc. Natl. Acad. Sci. USA,* 74, 5463 (1977)] or a method comprising the use of an apparatus for nucleotide sequence analysis such as 373A•DNA Sequencer (manufactured by Perkin-Elmer).

Based on the nucleotide sequence thus determined, the DNA of interest can also be prepared by chemical synthesis using, for example, DNA Synthesizer 8905 manufactured by Perceptive Biosystems or the like.

The vector into which the DNA of the present invention is ligated includes pBluescript II KS(+) (manufactured by Stratagene), pDIRECT [*Nucleic Acids Res.,* 18, 6069 (1990)], pCR-Script Amp SK (+) (manufactured by Stratagene), pT7Blue manufactured by Novagen), pCR II (manufactured by Invitrogen), pCR-TRAP (manufactured by Genehunter) and the like.

A recombinant DNA pPM1139SK which comprises the DNA comprising the nucleotide sequence represented by SEQ ID NO:2 has been deposited on Sep. 13, 2001, as FERM BP-7732, in International Patent Organism Depositary, National Institute of Advanced Industrial Science and Technology (Central 6, 1-1, Higashi 1-Chome Tsukuba, Ibaraki, 305-8566, Japan).

The microorganism containing the recombinant DNA which comprises the DNA comprising the sequence represented by SEQ ID NO:2 includes *Escherichia coli* and the like.

*Escherichia coli* includes *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Escherichia coli* MP347, *Escherichia coli* NM522, *Escherichia coli* ME8415 and the like.

Any method can be used in the introduction method of the recombinant DNA, so long as it is a method for introducing DNA into the host cell. Examples include the method using a calcium ion [*Proc. Natl. Acad. Sci. USA,* 69, 2110 (1972)], the protoplast method (Japanese Published Unexamined Patent Application No. 248394/88), electroporation [*Nucleic Acid Res.,* 16, 6127 (1988)] and the like.

*Escherichia coli* containing the recombinant DNA which comprises the DNA comprising the nucleotide sequence represented by SEQ ID NO:2 includes *Escherichia coli* NM522/pPM1139.

[2] Preparation of the Protein of the Present Invention

The protein having α1,4-galactosyltransferase activity can be produced by expressing the DNA obtained by the method of the above item [1] in a host cell, for example, as shown below, by using a method described in *Molecular Cloning*, Second Edition, *Current Protocols in Molecular Biology* or the like.

Based on the above DNA, a DNA fragment of an appropriate length containing a portion which encodes the protein can be prepared, if necessary. In addition, productivity of the protein can be improved by substituting a nucleotide in the nucleotide sequence of the protein-coding region so that it has the most suitable codons for the expression in the host.

A recombinant DNA is prepared by inserting the DNA into a downstream of the promoter of an appropriate expression vector.

A transformant capable of producing the protein used for the process of the present invention can be obtained by introducing the recombinant DNA into a host cell suitable for the expression vector.

Any bacteria, yeasts, animal cells, insect cells, plant cells and the like can be used as the host cell, so long as it can express the gene of interest.

The expression vectors include those which can replicate autonomously in the above host cell or those which can be integrated into a chromosome and have a promoter at such a position that the DNA used in the production process of the present invention can be transcribed.

When a procaryote such as bacterium is used as the host cell, it is preferred that the recombinant DNA which comprises the DNA encoding the protein of the present invention can replicate autonomously in the procaryote, and that the recombinant vector contains a promoter, a ribosome binding sequence, the DNA of the present invention and a transcription termination sequence. The vector may further comprise a gene regulating the promoter.

The expression vector includes pHelix1 (manufactured by Roche Diagnostics), pKK233-2 (manufactured by Amersham Pharmacia Biotech), pSE280 (manufactured by Invitrogen), pGEMEX-1 (manufactured by Promega), pQE-8 (manufactured by QIAGEN), pET-3 (manufactured by Novagen), pKYP10 (Japanese Published Unexamined Patent Application No. 110600/83), pKYP200 [*Agric. Biol. Chem.,* 48, 669 (1984)], pLSA1 [*Agric. Biol. Chem.,* 53, 277 (1989)], pGEL1 [*Proc. Natl. Acad. Sci. USA,* 82, 4306 (1985)], pBluescript II SK(+), pBluescript II KS(−) (manufactured by Stratagene), pTrS30 [prepared from *Escherichia coli* JM109/pTrS30 (FERM BP-5407)], pTrS32 [prepared from *Escherichia coli* JM109/pTrS32 (FERM BP-5408)], pPAC31 (WO98/12343), pUC19 [*Gene,* 33, 103 (1985)], pSTV28 (manufactured by Takara Shuzo), pUC118 (manufactured by Takara Shuzo), pPA1 (Japanese Published Unexamined Patent Application No. 233798/88) and the like.

Any promoter can be used, so long as it can function in the host cell. Examples include promoters derived from *Escherichia coli*, phage and the like, such as trp promoter ($P_{trp}$), lac promoter ($P_{lac}$), $P_L$ promoter, $P_R$ promoter and $P_{SE}$ promoter, SPO1 promoter, SPO2 promoter, penP promoter and the like. Also, artificially designed and modified promoters, such as a promoter in which two $P_{trp}$ are linked in tandem, tac promoter, lacT7 promoter and letI promoter, can be used.

It is preferred to use a plasmid in which the space between Shine-Dalgarno sequence, which is the ribosome binding sequence, and the initiation codon is adjusted to an appropriate distance (for example, 6 to 18 nucleotides).

The transcription termination sequence to express the DNA used in the production process of the present invention is not essential for the recombinant DNA. However, it is preferred to lie a transcription terminating sequence immediately downstream of the structural gene.

The procaryotes include microorganisms belonging to the genera *Escherichia, Serratia, Bacillus, Brevibacterium, Corynebacterium, Microbacterium, Pseudomonas* and the like. Examples include *Escherichia coli* XL1-Blue, *Escherichia coli* XL2-Blue, *Escherichia coli* DH1, *Escherichia coli* NM522, *Escherichia coli* MC1000, *Escherichia coli* KY3276, *Escherichia coli* W1485, *Escherichia coli* JM109,

*Escherichia coli* HB101, *Escherichia coli* No. 49, *Escherichia coli* W3110, *Escherichia coli* NY49, *Serratia ficaria*, *Serratia fonticola*, *Serratia liquefaciens*, *Serratia marcescens*, *Bacillus subtilis*, *Bacillus amyloliquefaciens*, *Brevibacterium immariophilum* ATCC 14068, *Brevibacterium saccharolyticum* ATCC 14066, *Corynebacterium ammoniagenes*, *Corynebacterium glutamicum* ATCC 13032, *Corynebacterium glutamicum* ATCC 14067, *Corynebacterium glutamicum* ATCC 13869, *Corynebacterium acetoacidophilum* ATCC 13870, *Microbacterium ammoniaphilum* ATCC 15354, *Pseudomonas* sp. D-0110 and the like.

Introduction of the recombinant DNA can be carried out by any methods for introducing DNA into the above-described host cells, such as the method using a calcium ion [*Proc. Natl. Acad. Sci. USA*, 69, 2110 (1972)], the protoplast method (Japanese Published Unexamined Patent Application No. 248394/88) and electroporation [*Nucleic Acids Res.*, 16, 6127 (1988)].

When a yeast cell is used as the host cell, the expression vector includes YEp13 (ATCC 37115), YEp24 (ATCC 37051), YCp50 (ATCC 37419), pHS19, pHS15 and the like.

Any promoter can be used so long as it can function in yeast. Examples include PHO5 promoter, PGK promoter, GAP promoter, ADH promoter, gal 1 promoter, gal 10 promoter, a heat shock polypeptide promoter, MF$\alpha$1 promoter, CUP 1 promoter and the like.

The host cell includes yeast strain belonging to the genera *Saccharomyces*, *Schizosaccharomyces*, *Kluyveromyces*, *Trichosporon*, *Schwanniomyces*, *Pichia*, *Candida* and the like. Examples include *Saccharomyces cerevisiae*, *Schizosaccharomyces pombe*, *Kluyveromyces lactis*, *Trichosporon pullulans*, *Schwanniomyces alluvius*, *Pichia pastoris*, *Candida utilis* and the like.

Introduction of the recombinant DNA can be carried out by any of the methods for introducing DNA into yeast, such as electroporation [*Methods. Enzymol.*, 194, 182 (1990)], the spheroplast method [*Proc. Natl. Acad. Sci. USA*, 81, 4889 (1984)] and the lithium acetate method [*J. Bacteriol.*, 153, 163 (1983)].

When an animal cell is used as the host, the expression vector includes pcDNAI (available from Funakoshi) and pcDM8 (available from Funakoshi), pAGE107 (Japanese Published Unexamined Patent Application No. 22979/91), pAS3-3 (Japanese Published Unexamined Patent Application No. 227075/90), pcDNAI/Amp (manufactured by Invitrogen), pREP4 (manufactured by Invitrogen), pAGE103 [*J. Biochem.*, 101, 1307 (1987)], pAGE210, pAMo, pAMoA and the like.

Any promoter can be used, so long as it can function in an animal cell. Examples include a promoter of IE (immediate early) gene of cytomegalovirus (CMV), SV40 early promoter, a metallothionein promoter, a promoter of retrovirus, a heat shock promoter, SR$\alpha$ promoter and the like. Also, the enhancer of the IE gene of human CMV can be used together with the promoter.

The host cell includes mouse myeloma cell, rat myeloma cell, mouse hybridoma cell, human Namalwa cell, Namalwa KJM-1 cell, human fetal kidney cell, human leukemia cell, African grivet kidney cell, Chinese hamster ovary (CHO) cell, HST5637 (Japanese Published Unexamined Patent Application No. 299/88) and the like.

The mouse myeloma cell includes SP2/0, NS0 and the like. The rat myeloma cell includes YB2/0 and the like. The human fetal kidney cell includes HEK293 (ATCC: CRL-1573) and the like. The human leukemia cell includes BALL-1 and the like. The African grivet kidney cell includes COS-1, COS-7 and the like.

Introduction of the recombinant DNA into animal cells can be carried out by any of methods for introducing DNA into animal cells, such as electroporation [*Cytotechnology*, 3, 133 (1990)], the calcium phosphate method (Japanese Published Unexamined Patent Application No. 227075/90), the lipofection method [*Proc. Natl. Acad. Sci. USA*, 84, 7413 (1987)], and the method described in *Virology*, 52, 456 (1973).

When an insect cell is used as the host, the protein can be produced by a known method described in, for example, *Baculovirus Expression Vectors, A Laboratory Manual*, W.H. Freeman and Company, New York (1992), *Molecular Biology, A Laboratory Manual, Current Protocols in Molecular Biology*, *Bio/Technology*, 6, 47 (1988) or the like.

Specifically, a recombinant gene transfer vector and baculovirus are co-transfected into an insect cell to obtain a recombinant virus in a supernatant of the culture of its insect cell, and then an insect cell is infected with the resulting recombinant virus to produce the protein.

The transfer vector used in the method includes pVL1392, pVL1393 and pBlueBacIII (all manufactured by Invitrogen), and the like.

The baculovirus includes *Autographa californica* nuclear polyhedrosis virus which infects insects of the family Barathra and the like.

The insect cell includes *Spodoptera frugiperda* ovary cell, *Trichoplusia ni* ovary cell, silkworm ovary-derived culturing cell and the like.

*Spodoptera frugiperda* ovary cell includes Sf9 and Sf21 (*Baculovirus Expression Vectors, A Laboratory Manual*) and the like. *Trichoplusia ni* ovary cell includes High 5 and BTI-TN-5B1-4 (manufactured by Invitrogen) and the like. The cell line derived from silkworm ovary cell includes *Bombyx mori* N4 and the like.

The method for co-transfecting the above transfer vector and the above baculovirus for the preparation of the recombinant virus includes the calcium phosphate method (Japanese Published Unexamined Patent Application No. 227075/90), the lipofection method [*Proc. Natl. Acad. Sci. USA*, 84, 7413 (1987)] and the like.

When a plant cell is used as the host cell, the expression vector includes Ti plasmid, a tobacco mosaic virus vector, and the like.

As the promoter, any promoter can be used, so long as it can function in a plant cell. Examples include 35S promoter of cauliflower mosaic virus (CaMV), rice actin 1 promoter and the like.

The host cell includes a plant cell and the like, such as tobacco, potato, tomato, carrot, soybean, rape, alfalfa, rice, wheat and barley.

Introduction of the recombinant vector is carried out by any of methods for introducing DNA into a plant cell, such as *Agrobacterium* method (Japanese Published Unexamined Patent Application No. 140885/84, Japanese Published Unexamined Patent Application No. 70080/85, WO 94/00977), electroporation (Japanese Published Unexamined Patent Application No. 251887/85) and the method using a particle gun (Japanese Patent Nos. 2606856 and 2517813).

The protein having $\alpha$1,4-galactosyltransferase activity can be produced by culturing the transformant thus obtained in a medium to produce and accumulate the protein having $\alpha$1,4-galactosyltransferase activity in the culture, and recovering it from the culture.

Culturing of the transformant used in the process production of the present invention in a medium is carried out according to the conventional method as used in culturing of the host.

As a medium for culturing the transformant obtained by using, as the host, prokaryote such as *Escherichia coli*, or eukaryote such as yeast, either a natural medium or a synthetic medium may be used, so long as it contains a carbon source, a nitrogen source, an inorganic salt and the like which can be assimilated by the organism and the transformant can be cultured efficiently.

Any carbon source can be used, so long as the organism can assimilate, and it includes carbohydrates, such as glucose, fructose, sucrose, molasses containing them, starch and starch hydrolysate; organic acids, such as acetic acid and propionic acid; alcohols, such as ethanol and propanol; and the like.

The nitrogen source includes ammonia, various ammonium salts of inorganic acids or organic acids, such as ammonium chloride, ammonium sulfate, ammonium acetate and ammonium phosphate; other nitrogen-containing compounds; peptone; meat extract; yeast extract; corn steep liquor; casein hydrolysate; soybean meal and soybean meal hydrolysate; various fermented cells and digested matter thereof; and the like.

The inorganic salt includes potassium dihydrogen phosphate, dipotassium hydrogen phosphate, magnesium phosphate, magnesium sulfate, sodium chloride, ferrous sulfate, manganese sulfate, copper sulfate, calcium carbonate and the like.

Culturing is usually carried out under aerobic conditions by shaking culture, submerged spinner culture under aeration or the like. The culturing temperature is preferably from 15 to 40° C., and the culturing time is generally from 5 hours to 7 days. The pH of the medium is preferably maintained at 3.0 to 9.0 during the culturing. The pH can be adjusted using inorganic or organic acid, an alkali solution, urea, calcium carbonate, ammonia or the like.

Also, antibiotics, such as ampicillin and tetracycline, can be added to the medium during culturing, if necessary.

When a microorganism transformed with an expression vector containing an inducible promoter is cultured, an inducer can be added to the medium, if necessary. For example, isopropyl-β-D-thiogalactopyranoside or the like can be added to the medium when a microorganism transformed with an expression vector containing lac promoter is cultured; or indoleacrylic acid or the like can be added thereto when a microorganism transformed with an expression vector containing trp promoter is cultured.

The medium for culturing a transformant obtained using an animal cell as the host includes generally used RPMI 1640 medium [*The Journal of the American Medical Association*, 199, 519 (1967)], Eagle's MEM medium [*Science*, 122, 501 (1952)], DMEM medium [*Virology*, 8, 396 (1959)], and 199 Medium [*Proceeding of the Society for the Biological Medicine*, 73, 1 (1950)], as well as media to which fetal calf serum or the like has been added to the above media and the like.

Culturing is generally carried out at pH 6 to 8 and at 25 to 40° C. for 1 to 7 days in the presence of 5% $CO_2$ or the like.

Furthermore, if necessary, antibiotics such as kanamycin, penicillin and streptomycin, can be added to the medium during the culturing.

The medium for culturing a transformant obtained using an insect cell as the host includes generally used TNM-FH medium (manufactured by Pharmingen), Sf-900 II SFM (manufactured by Life Technologies), ExCell 400 and ExCell 405 (both manufactured by JRH Biosciences), Grace's Insect Medium [*Nature*, 195, 788 (1962)] and the like.

Culturing is generally carried out at pH 6 to 7 and at 25 to 30° C. for 1 to 5 days or the like.

Furthermore, if necessary, antibiotics such as gentamicin can be added to the medium during the culturing.

A transformant obtained by using a plant cell as the host cell can be used as the cell or after differentiating to a plant cell or organ. The medium used in the culturing of the transformant includes Murashige and Skoog (MS) medium, White medium, media to which a plant hormone, such as auxin or cytokinine, has been added, and the like.

Culturing is carried out generally at a pH 5 to 9 and at 20 to 40° C. for 3 to 60 days.

Also, antibiotics, such as kanamycin and hygromycin, can be added to the medium during the culturing, if necessary.

As described above, the protein having α-1,4-galactosyltransferase activity can be produced by culturing a transformant derived from a microorganism, animal cell, insect cell or plant cell containing the recombinant DNA which comprises the DNA encoding the protein according to the general culturing method to produce and accumulate the protein, and recovering the protein from the culture.

In the production of the protein having α1,4-galactosyltransferase activity, the protein can be produced so as to have a structure as it is or can be produced as a secretory protein having a signal sequence or a fusion protein according to the method described in *Molecular Cloning*, Second Edition and the like The protein to be fused includes β-galactosidase, protein A, IgG binding region of protein A, chloramphenicol acetylransferase, poly(Arg), poly(Glu), protein G, maltose binding protein, glutathione S-transferase, polyhistidine chain (His-tag), S peptide, DNA binding protein domain, Tac antigen, thioredoxin, green fluorescent protein, FLAG peptide, epitope of any antibody, and the like [Akio Yamakawa, *Experimental Medicine (Jikken Igaku)*, 13, 469-474 (1995)].

Furthermore, the process for producing the protein having α1,4-galactosyltransferase activity includes a process for production in which the protein is produced on an outer membrane of the host cell, and the process for production can be selected by changing the host cell used or the structure of the protein produced.

When the protein having α1,4-galactosyltransferase activity is produced in a host cell or on an outer membrane of the host cell, the produced protein can be actively secreted extracellularly according to, for example, the method of Paulson et al. [*J. Biol. Chem.*, 264, 17619 (1989)], the method of Lowe et al. [*Proc. Natl. Acad. Sci. USA*, 86, 8227 (1989); *Genes Develop.*, 4, 1288 (1990)], or the methods described in Japanese Published Unexamined Patent Application No. 336963/93, WO94/23021, and the like.

Specifically, the protein of the present invention can be actively secreted extracellularly by producing it in the form that a signal peptide has been added to the side of N-terminal of a protein containing an active site of the protein having α1,4-galactosyltransferase activity according to the recombinant DNA technique.

Furthermore, the protein production can be increased utilizing a gene amplification system using a dihydrofolate reductase gene or the like according to the method described in Japanese Published Unexamined Patent Application No. 227075/90.

Moreover, the protein having α1,4-galactosyltransferase activity can be produced by redifferentiating a gene-introduced animal or plant cell to develop a gene-introduced transgenic animal individual (transgenic nonhuman animal) or plant individual (transgenic plant), and using the individual.

When the transformant is the animal individual or plant individual, the protein can be produced by breeding or cultivating it to produce and accumulate the protein, and recovering the protein from the animal individual or plant individual.

The process for producing the protein having α1,4-galactosyltransferase activity using the animal individual includes a method for producing the protein of the present invention in a nonhuman animal developed by introducing a gene according to a known method [*Am. J. Clin. Nutr.,* 63, 639S (1996), *Am. J. Clin. Nutr.,* 63, 627S (1996), *Bio/Technology,* 9, 830 (1991)].

In the animal individual, the protein can be produced by breeding a transgenic nonhuman animal to which the DNA encoding the protein having α1,4-galactosyltransferase has been introduced to produce and accumulate the protein in the animal, and recovering the protein from the animal. The protein produced in the animal is accumulated in milk (Japanese Published Unexamined Patent Application No. 309192/88), egg, and the like. Any promoter can be used, so long as it can function in the animal. Suitable examples include an α-casein promoter, a β-casein promoter, a β-lactoglobulin promoter, a whey acidic protein promoter, and the like, which are specific for mammary glandular cells.

The process for producing the protein having α-1,4-galactosyltransferase activity using the plant individual includes a process for producing the protein by cultivating a transgenic plant to which the DNA encoding the protein of the present invention is introduced by a known method [*Tissue Culture (Soshiki Baiyo),* 20 (1994), *Tissue Culture (Soshiki Baiyo),* 21 (1995), *Trends Biotechnol.,* 15, 45 (1997)] to produce and accumulate the protein in the plant, and recovering the protein from the plant.

The protein produced by the production process of the protein of the present invention can be isolated and purified by using the general method for isolating and purifying an enzyme.

For example, when the protein having 1,4-galactosyltransferase activity is produced as a soluble product in the host cells, the cells are collected by centrifugation after culturing, suspended in an aqueous buffer, and disrupted using an ultrasonicator, a French press, a Manton Gaulin homogenizer, a Dynomill, or the like to obtain a cell-free extract.

From the supernatant obtained by centrifuging the cell-free extract, a purified product can be obtained by the general method used for isolating and purifying an enzyme, for example, solvent extraction, salting-out using ammonium sulfate or the like, desalting, precipitation using an organic solvent, anion exchange chromatography using a resin such as diethylaminoethyl (DEAE)-Sepharose or DIAION HPA-75 (manufactured by Mitsubishi Chemical), cation exchange chromatography using a resin such as S-Sepharose FF (manufactured by Pharmacia), hydrophobic chromatography using a resin such as butyl sepharose or phenyl sepharose, gel filtration using a molecular sieve, affinity chromatography, chromatofocusing, or electrophoresis such as isoelectronic focusing, alone or in combination thereof.

When the protein is produced as an inclusion body in the host cells, the cells are collected in the same manner, disrupted and centrifuged to recover the protein as the precipitate fraction, and then the inclusion body of the protein is solubilized with a protein-denaturing agent.

The solubilized solution is diluted or dialyzed in a solution free from a protein denaturing agent or a solution having a diluted concentration of a protein denaturing agent in such a degree that the protein is not denatured to thereby constitute the normal tertiary structure of the protein, and then a purified product of the protein can be obtained by a purification/isolation method similar to the above.

When the protein having α1,4-galactosyltransferase activity or derivatives such as its glycosylated-derivatives are secreted out of cells, the protein or its derivatives such as the glycosylated-derivatives can be collected in the culture supernatant.

Specifically, the culture medium is treated in a manner similar to the above, such as centrifugation to obtain a solubilized fraction, from which a purified product can be obtained using a purification/isolation method similar to the above.

The protein obtained by the above method includes a protein comprising the amino acid sequence represented by SEQ ID NO:1.

Furthermore, the protein having α1,4-galactosyltransferase activity is produced as a fusion protein with other protein, and can be purified using affinity chromatography using a substance having affinity to the fusion protein. For example, the fusion protein having α1,4-galactosyltransferase activity is produced as a fusion protein with protein A according to the method of Lowe et al. [*Proc. Natl. Acad. Sci. USA,* 86, 8227 (1989); *Genes Develop.,* 4, 1288 (1990)], or the method described in Japanese Published Unexamined Patent Application No. 336963/93 or WO94/23021, and the fusion protein can be purified by affinity chromatography using immunoglobulin G.

Moreover, the protein having α1,4-galactosyltransferase activity is produced as a fusion protein with Flag peptide, and the fusion protein can be purified by affinity chromatography using an anti-Flag antibody [*Proc. Natl. Acad. Sci., USA,* 86, 8227 (1989), *Genes Develop.,* 4, 1288 (1990)]. In addition, purification can be carried out by affinity chromatography using the antibody against the polypeptide per se.

Based on the amino acid sequence information of the protein thus obtained, the protein having α1,4-galactosyltransferase can be produced by a chemical synthesis method, such as Fmoc (fluorenylmethyloxycarbonyl)method or tBoc (t-butyloxycarbonyl)method. It can also be chemically synthesized using a peptide synthesizer manufactured by Advanced ChemTech, Perkin-Elmer, Pharmacia, Protein Technology Instrument, Synthecell-Vega, PerSeptive, Shimadzu, Corporation, or the like.

(3) Preparation of Galactose-containing Complex Carbohydrate

A galactose-containing complex carbohydrate can be produced in an aqueous medium by allowing a culture of the transformant obtained by the culturing described in the above item [2] or a treated product of the culture as an enzyme source, uridine-5'-diphosphogalactose and an acceptor complex carbohydrate to be present in the aqueous medium to produce and accumulate the galactose-containing complex carbohydrate in the aqueous medium.

The treated product of the culture includes a concentrated product of the culture, a dried product of the culture, cells obtained by centrifuging the culture, a dried product of the cells, a freeze-dried product of the cells, a surfactant-treated product of the cells, an ultrasonic-treated product of the cells, a mechanically disrupted product of the cells, a solvent-treated product of the cells, an enzyme-treated product of the cells, a protein fraction of the cells, an immobilized product of the cells, an enzyme preparation obtained by extracting from the cell, and the like.

The acceptor complex carbohydrate used in the production of the galactose-containing complex carbohydrate is a complex carbohydrate comprising an oligosaccharide having galactose in its non-reducing terminal, preferably a complex carbohydrate comprising an oligosaccharide having a struc- 
ture selected from the group consistnig of lactose, N-acetyllactosamine, lacto-N-tetraose, para-lacto-N-neohexaose and lacto-N-neotetraose in the non-reducing terminal, and more preferably a complex carbohydrate selected from the group consisting of lactose, N-acetyllactosamine, lacto-N-tetraose, para-lacto-N-neohexaose and lacto-N-neotetraose.

The enzyme source used in the production of the galactose-containing complex carbohydrate is used in a concentration of 1 mU/l to 1,000 U/l, preferably 10 mU/l to 500 U/l, when the activity capable of forming 1 μmol of galactose-containing complex carbohydrate at 37° C. in 1 minute is defined as 1 unit (U).

The aqueous medium used in the production of the galactose-containing complex carbohydrate includes water; a buffer such as a phosphate buffer, a carbonate buffer, an acetate buffer, a borate buffer, a citrate buffer and a tris buffer; alcohol, such as methanol and ethanol; ester such as ethyl acetate; ketone such as acetone; amide such as acetamide; and the like. Also, the culture of the microorganisms used as the enzyme source can be used as an aqueous medium.

In the production of the galactose-containing complex carbohydrate, a surfactant or an organic solvent may be added, if necessary. Any surfactant capable of accelerating the formation of a galactose-containing complex carbohydrate can be used as the surfactant. Examples include nonionic surfactants such as polyoxyethylene octadecylamine (e.g., Nymeen S-215, manufactured by Nippon Oil & Fats); cationic surfactants, such as cetyltrimethylammonium bromide and alkyldimethyl benzylammoniumchloride (e.g., Cation F2-40E, manufactured by Nippon Oil & Fats); anionic surfactants such as lauroyl sarcosinate; tertiary amines such as alkyldimethylamine (e.g., Tertiary Amine FB, manufactured by Nippon Oil & Fats); and the like, which are used alone or as a mixture of two or more. The surfactant is used generally in a concentration of 0.1 to 50 g/l. The organic solvent includes xylene, toluene, fatty acid alcohol, acetone, ethyl acetate, and the like, which are used in a concentration of generally 0.1 to 50 ml/l.

The production reaction for the galactose-containing complex carbohydrate is carried out in an aqueous medium having a pH 5 to 10, preferably pH 6 to 8, at 20 to 50° C. for 1 to 96 hours. In the production reaction, inorganic salts, such as $MnCl_2$ and $MgCl_2$, can be added, if necessary.

The amount of the galactose-containing complex carbohydrate produced in the aqueous medium can be determined, for example, using a carbohydrate analysis system manufactured by Dionex [*Anal. Biochem.,* 189:, 151 (1990)] or the like.

The galactose-containing complex carbohydrate produced in the aqueous medium can be recovered by the ordinary method using activated carbon, an ion exchange resin or the like.

Examples of the present invention are shown below; however, the present invention is not limited to these Examples.

BRIEF DESCRIPTION OF THE DRAWING

Also, in the drawing, $Amp^r$ represents an ampicillin-resistant gene; $P_{trp}$ represents tryptophane promoter; and pm1139 represents a gene encoding an α1,4-galactosyltransferase.

BEST MODE FOR CARRYING OUT THE INVENTION

EXAMPLE 1

Construction of a Strain Expressing a Gene Encoding α1,4-galactosyltransferase Derived from *Pasteurella multocida*

*Pasteurella multocida* PM70 was cultured by a known method [*FEMS Microbiol. Lett.,* 166, 289 (1998)].

After the culturing, a chromosomal DNA of the microorganism was isolated and purified by the method described in *Current Protocols in Molecular Biology.*

Using DNA fragments having the nucleotide sequences represented by SEQ ID NOs:3 and 4 which had been synthesized by using a DNA synthesizer Model 8905 manufactured by Perceptive Biosystems, a DNA fragment containing pm1139 considered to be a gene encoding an α1,4-galactose transferase in the full nucleotide sequence of the genomic DNA in *Pasteurella multocida* PM70 was amplified by the following method.

PCR was carried out by using the above synthetic DNA fragments as a primer set and using the chromosomal DNA of *Pasteurella multocida* PM70 as the template. The PCR was carried out by using 40 μl of a reaction solution containing 0.1 μg of the chromosomal DNA, 0.5 μmol/l of each of the primers, 2.5 units of Pfu DNA polymerase (manufactured by Stratagene), 4 μl of 10× buffer solution for Pfu DNA polymerase and 200 μmol/l of each deoxy NTP, and repeating 30 times of a step consisting of 1 minute at 94° C., 2 minutes at 42° C. and 3 minutes at 72° C.

A 1/10 volume of the reaction solution was subjected to agarose gel electrophoresis to confirm that the fragment of interest was amplified, and then the remaining reaction solution was mixed with the same volume of TE [10 mmol/l Tris-HCl and 1 mmol/l EDTA (pH 8.0)] saturated phenol/chloroform (1 vol/1 vol).

After the mixed solution was centrifuged, the thus obtained upper layer was mixed with 2 volumes of cold ethanol and allowed to stand at −80° C. for 30 minutes. A precipitate of DNA was obtained by centrifuging the solution.

The DNA precipitate was dissolved in 20 μl of TE.

Using 5 μl of the dissolved solution, the DNA was digested with restriction enzymes HindIII and BamHI, the resulting DNA fragments were separated by agarose gel electrophoresis, and then a DNA fragment of 0.9 kb was recovered by using Gene Clean II Kit (purchased from Funakoshi).

After 0.2 μg of pBluescript II SK(+) was digested with restriction enzymes HindIII and BamHI, the resulting DNA fragments were separated by agarose gel electrophoresis, and then a DNA fragment of 2.9 kb was recovered in the same manner.

Using a ligation kit (manufactured by Takara Shuzo), the 0.9 kb and 2.9 kb fragments were subjected to ligation reaction at 16° C. for 16 hours. *Escherichia coli* NM522 was transformed by using the ligation reaction solution in accordance with the above known method, and the transformant was spread on an LB agar medium [10 g/l Bacto-Tryptone (manufactured by Difco), 10 g/l yeast extract (manufactured by Difco), 5 g/l sodium chloride and 15 g/l agarose] containing 50 μg/ml ampicillin, followed by culturing overnight at 30° C.

A plasmid was extracted from the thus formed transformant colonies in accordance with the above known method, the structure of the plasmid was confirmed by restriction enzyme digestion, and the plasmid was named pPM1139SK.

The plasmid pPM1139SK has been deposited on Sep. 13, 2001, as FERM BP-7732 in International Patent Organism Depositary, National Institute of Advanced Industrial Science and Technology (postal code 305-8566; Central 6, 1-1-1 Higashi, Tsukuba, Ibaraki, Japan).

Next, pPM1139SK was digested with restriction enzymes HindIII and BamHI, the resulting DNA fragments were separated by agarose gel electrophoresis, and then a DNA fragment of 0.9 kb was recovered. After 0.2 μg of pTrS31 DNA was digested with restriction enzymes HindIII and BamHI, the resulting DNA fragments were separated by agarose gel electrophoresis, and then a DNA fragment of 4.3 kb was recovered in the same manner.

Using the ligation kit, the 0.9 kb and 4.3 kb fragments was subjected to ligation reactoin at 16° C. for 16 hours.

*Escherichia coli* NM522 was transformed by using the ligation reaction solution in accordance with the above known method, and the transformant was spread on the LB agar medium containing 50 μg/ml ampicillin, followed by culturing overnight at 30° C.

Figure 1:
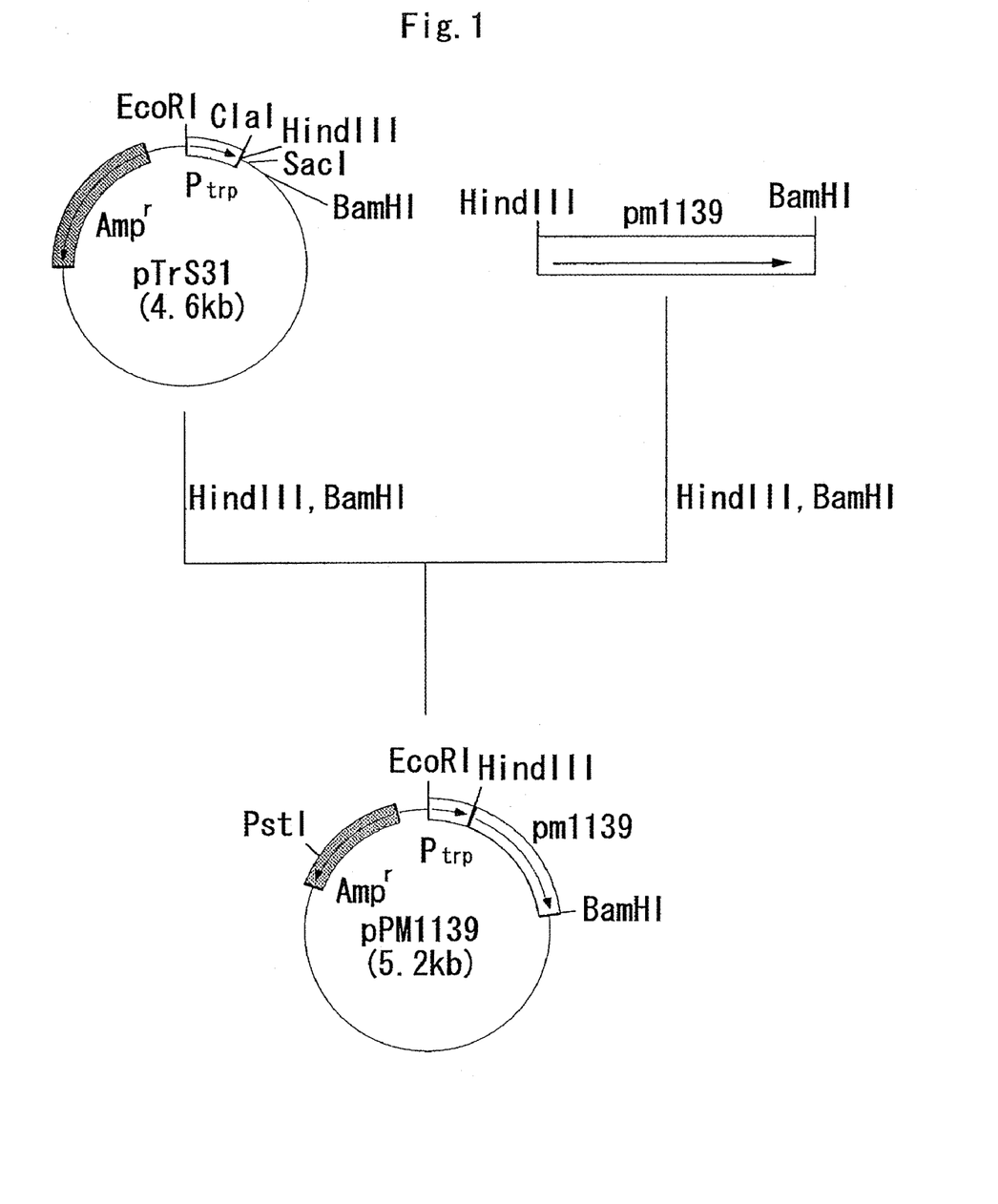
FIG. 1 shows construction steps of α1,4-galactosyltransferase gene expression plasmid pPM1139.

A plasmid was extracted from the thus formed transformant colonies in accordance with the above known method, thereby obtaining an expression plasmid pPM1139. The structure of the plasmid was verified by restriction enzyme digestion (FIG. 1).

EXAMPLE 2

Production of Galα-1,4Galβ1,4Glc

*Escherichia coli* NM522/pPM1139 obtained in Example 1 was inoculated into a test tube charged with 8 ml of LB medium containing 50 μg/ml ampicillin, followed by culturing at 28° C. for 17 hours.

The culture was inoculated into a test tube charged with 8 ml of LB medium containing 50 μg/ml ampicillin, with an inoculum size of 1%, followed by culturing at 37° C. for 7 hours. Wet cells were obtained by centrifuging 0.1 ml of the culture. The wet cells can be stored at −20° C., if necessary, and it was able to use them by thawing prior to use.

The reaction was carried out at 37° C. for 10 hours in 0.1 ml of a reaction solution containing the NM522/pPM1139 wet cells (prepared from 0.1 ml of the culture), 50 mmol/l citrate buffer (pH 7.0), 10 mmol/l $MnCl_2$, 10 mmol/l lactose, 10 mmol/l UDP-galactose and 4 g/l Nymeen S-215.

After completion of the reaction, the reaction product was analyzed by using a sugar analyzer manufactured by Dionex (DX-500) under the following analyzing conditions to confirm that 7.6 mmol/l (3840 mg/l) of Galα1,4Galβ1,4Glc was formed and accumulated in the reaction solution.

Analyzing Conditions:
Column: CarboPAC PA10
Eluent: eluent A; $H_2O$, eluent B; 500 mmol/l NaOH
Gradient: Linear gradient from a composition of 8% eluent B at 0 minute to a composition of 20% eluent B spending 21 minutes.
Detector: Pulsed amperometry detector

EXAMPLE 3

Examination on Substrate Specificity

*Escherichia coli* NMS22/pPM1139 obtained in Example 1 was inoculated into a test tube charged with 8 ml of LB medium containing 50 μg/ml ampicillin, followed by culturing at 28° C. for 17 hours.

The culture was inoculated into a test tube charged with 8 ml of LB medium containing 50 μg/ml ampicillin, with an inoculum size of 1%, followed by culturing at 37° C. for 7 hours. Wet cells were obtained by centrifuging 0.1 ml of the culture. The wet cells can be stored at −20° C., if necessary, and it was able to use them by thawing prior to use.

Also, a strain NM522/pGT5 derived from *Neisseria gonorrhoeae* in which an α1,4-galactose transferase is expressed, which had been prepared in accordance with the method described in a reference [*Nat. Biotechnol.*, 16, 847 (1998)], was inoculated into a test tube charged with 8 ml of LB medium containing 50 μg/ml ampicillin, followed by culturing at 28° C. for 17 hours. The culture was inoculated into a test tube charged with 8 ml of LB medium containing 50 μg/ml ampicillin, with an inoculum size of 1%, followed by culturing at 30° C. for 4 hours and then at 40° C. for 3 hours, respectively. Wet cells were obtained by centrifuging 0.1 ml of the culture. The wet cells can be stored at −20° C., if necessary, and it was able to use them by thawing prior to use.

The reaction was carried out at 37° C. for 17 hours in 0.1 ml of a reaction solution containing 50 mmol/l citrate buffer (pH 7.0), 10 mmol/l $MnCl_2$, 10 mmol/l each receptor substrate, 10 mmol/l UDP-galactose and 4 g/l Nymeen S-215, using the NM522/pPM1139 wet cells or NM522/pPGT5 wet cells obtained in the above as enzyme sources. As the receptor substrates, N-acetyllactosamine (LacNAc: Galβ1,4GlcNAc), lacto-N-neotetraose (LNnT: Galβ1,4GlcNAcβ1,3Galβ1, 4Glc), para-lacto-N-neohexaose (pLNnH: Galβ1, 4GlcNAcβ1,3Galβ1,4GlcNAcβ1,3Galβ1,4Glc) and lacto-N-tetraose (LNT: Galβ1,3GlcNAcβ1,3Galβ1,4Glc) were used, in addition to lactose (Lac: Galβ1,4Glc). As a result, when the formed amount of globotriose (Galβ1,4Galβ1, 4Glc) produced by carrying out the reaction using NM522/pPGT5 wet cells as the enzyme source, and lactose as the substrate, was defined as 100, compounds in which galactose was respectively α1,4-bound to the non-reducing terminal of the substrate were produced at respective ratios shown in Table 1.

TABLE 1

| Substrate | Production ratio of galactose-containing complex carbohydrate | |
| --- | --- | --- |
| | Strain pGT5 | Strain PM1139 |
| Lac | 100.0 | 129.6 |
| LacNAc | 8.5 | 100.5 |
| LNnT | 12.3 | 100.4 |
| pLNnH | 11.3 | 92.7 |
| LNT | 64.8 | 78.4 |

As a result, it was shown that a galactose-containing complex carbohydrate can be efficiently produced by using a protein having α1,4-galactosyltransferase activity derived from *Pasteurella multocida* in the case where LacNAc, LNnT or pLNnH is used as the substrate.

INDUSTRIAL APPLICABILITY

According to the present invention, an α1,4-galactosyltransferase can be produced in a large amount. Also, a galactose-containing complex carbohydrate can be produced efficiently by using the enzyme.

Free Text of Sequence Listing:
SEQ ID NO:3—Description of artificial sequence: Synthetic DNA
SEQ ID NO:4—Description of artificial sequence: Synthetic DNA

The invention claimed is:

1. A process for producing a galactose-containing complex carbohydrate, which comprises:

allowing (i) a culture of a cell capable of producing a protein comprising the amino acid sequence of SEQ ID NO:1, or a treated product of the culture as an enzyme source, (ii) uridine-5'-diphosphogalactose and (iii) an acceptor complex carbohydrate to be present in an aqueous medium to produce and accumulate the galactose-containing complex carbohydrate in the aqueous medium; and recovering the galactose-containing complex carbohydrate from the aqueous medium, wherein the treated product of the culture is selected from the group consisting of a concentrated product of the culture, a dried product of the culture, cells obtained by centrifuging the culture, a dried product of the cells, a freeze-dried product of the cells, a surfactant-treated product of the cells, an ultrasonic-treated product of the cells, a mechanically disrupted product of the cells, a solvent-treated product of the cells, an enzyme-treated product of the cells, a protein fraction of the cells, an immobilized product of the cells and an enzyme preparation obtained by extracting from the cells, wherein the acceptor complex carbohydrate comprises an oligosaccharide having galactose in its non-reducing terminal.

2. The process according to claim 1, wherein the cell is a microorganism.

3. The process according to claim 2, wherein the microorganism is *Escherichia coli*.

4. The process according to any one of claims 1 to 3, wherein the oligosaccharide having galactose in the non-reducing terminal is selected from the group consisting of lactose, N-acetyllactosamine, lacto-N-tetraose, para-lacto-N-neohexaose and lacto-N-neotetraose.

5. A process for producing a galactose-containing complex carbohydrate, which comprises:

allowing (i) a culture of a cell which comprises a recombinant DNA comprising (a) a DNA comprising the nucleotide sequence of SEQ ID NO:2, or (b) a DNA which hybridizes on a filter with a DNA comprising the nucleotide sequence of SEQ ID NO:2 at 65° C. in the presence of 0.7-1.0 mol/l NaCl followed by washing the filter with 0.1× to 2×SSC solution at 65° C., and encodes a protein having α x 1,4-galactosyltransferase activity, or a treated product of the culture as an enzyme source, (ii) uridine-5'-diphosphogalactose and (iii) an acceptor complex carbohydrate to be present in an aqueous medium to produce and accumulate the galactose-containing complex carbohydrate in the aqueous medium; and recovering the galactose-containing complex carbohydrate from the aqueous medium, wherein the treated product of the culture is selected from the group consisting of a concentrated product of the culture, a dried product of the culture, cells obtained by centrifuging the culture, a dried product of the cells, a freeze-dried product of the cells, a surfactant-treated product of the cells, an ultrasonic-treated product of the cells, a mechanically disrupted product of the cells, a solvent-treated product of the cells, an enzyme-treated product of the cells, a protein fraction of the cells, an immobilized product of the cells and an enzyme preparation obtained by extracting from the cells, and wherein the acceptor complex carbohydrate comprises an oligosaccharide having galactose in its non-reducing terminal.

6. The process according to claim 5, wherein the cell is a microorganism.

7. The process according to claim 6, wherein the microorganism is *Escherichia coli*.

8. The process according to any one of claims 5 to 7, wherein the oligosaccharide having galactose in the non-reducing terminal is selected from the group consisting of lactose, N-acetyllactosamine, lacto-N-tetraose, para-lacto-N-neohexaose and lacto-N-neotetraose.

* * * * *

UNITED STATES PATENT AND TRADEMARK OFFICE
CERTIFICATE OF CORRECTION

PATENT NO. : 7,517,673 B2
APPLICATION NO. : 11/734869
DATED : April 14, 2009
INVENTOR(S) : Tetsuo Endo et al.

It is certified that error appears in the above-identified patent and that said Letters Patent is hereby corrected as shown below:

<u>COLUMN 1</u>:

Line 47, "4Galβ-1," should read --4-Galβ1,--.

<u>COLUMN 5</u>:

Line 62, "includes" should read --includes:--.

<u>COLUMN 18</u>:

Line 18, "able" should read --possible--; and
Line 31, "(Galβ1," should read --(Galα1,--.

<u>COLUMN 24</u>:

Line 27, "αx1,4-galactosyltransferase" should read
--α 1,4-galactosyltransferase--.

Signed and Sealed this

First Day of September, 2009

David J. Kappos
*Director of the United States Patent and Trademark Office*